(12) United States Patent
Werp et al.

(10) Patent No.: US 8,088,129 B2
(45) Date of Patent: * Jan. 3, 2012

(54) METHOD AND APPARATUS FOR MAGNETICALLY CONTROLLING MOTION DIRECTION OF MECHANICALLY PUSHED CATHETER

(75) Inventors: Peter R. Werp, St. Louis, MO (US); Walter M. Blume, St. Louis, MO (US); Francis M. Creighton, IV, St. Louis, MO (US); Rogers C. Ritter, Charlottesville, VA (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/628,711

(22) Filed: Dec. 1, 2009

(65) Prior Publication Data

US 2010/0174234 A1 Jul. 8, 2010

Related U.S. Application Data

(60) Continuation of application No. 10/288,231, filed on Nov. 5, 2002, now Pat. No. 7,625,382, which is a continuation of application No. 09/357,203, filed on Jul. 20, 1999, now Pat. No. 6,475,223, which is a division of application No. 08/920,446, filed on Aug. 29, 1997, now Pat. No. 6,015,414.

(51) Int. Cl.
*A61B 19/00* (2006.01)

(52) U.S. Cl. ............. 606/130; 606/108; 600/409
(58) Field of Classification Search ............ 606/108, 606/130; 600/424, 407, 434, 435, 410, 437, 600/411, 409; 128/898; 361/143, 152, 153, 361/154

See application file for complete search history.

(56) References Cited

U.S. PATENT DOCUMENTS

| | | | | |
|---|---|---|---|---|
| 3,674,014 A * | 7/1972 | Tillander | ........... | 600/434 |
| 5,125,888 A * | 6/1992 | Howard et al. | ........... | 600/12 |
| 5,654,864 A * | 8/1997 | Ritter et al. | ........... | 361/141 |
| 6,015,414 A * | 1/2000 | Werp et al. | ........... | 606/108 |
| 6,272,370 B1 * | 8/2001 | Gillies et al. | ........... | 600/411 |
| 7,625,382 B2 * | 12/2009 | Werp et al. | ........... | 606/108 |

* cited by examiner

*Primary Examiner* — Tuan Nguyen
(74) *Attorney, Agent, or Firm* — Harness, Dickey & Pierce, P.L.C.

(57) ABSTRACT

The movement of a catheter through a medium, which may be living tissue such as a human brain, is controlled by mechanically pushing a flexible catheter having a magnetic tip through the medium and applying a magnetic field having a magnitude and a direction that guides the mechanically-pushed catheter tip stepwise along a desired path. The magnetic field is controlled in a Magnetic Stereotaxis System by a processor using an adaptation of a PID (proportional, integral, and derivative) feedback method. The magnetic fields are applied by superconducting coils, and the currents applied through the coils are selected to minimize a current metric.

17 Claims, 3 Drawing Sheets

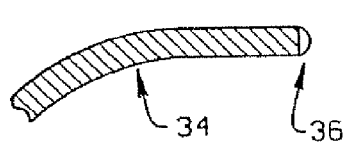
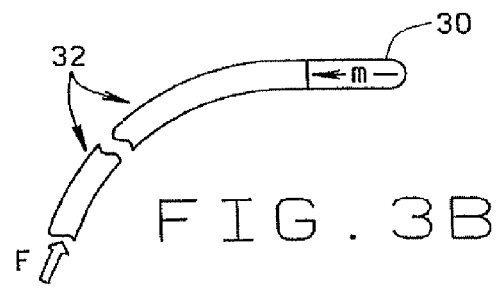
FIG. 3A
FIG. 3B
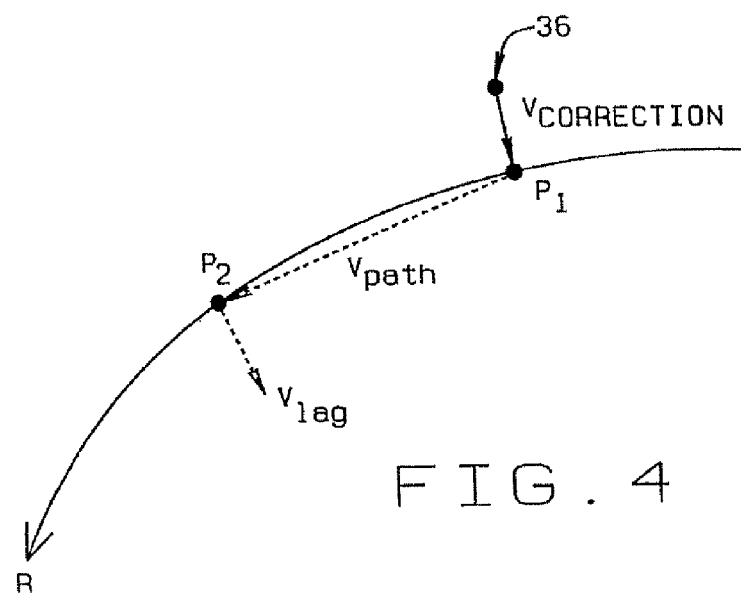
FIG. 4
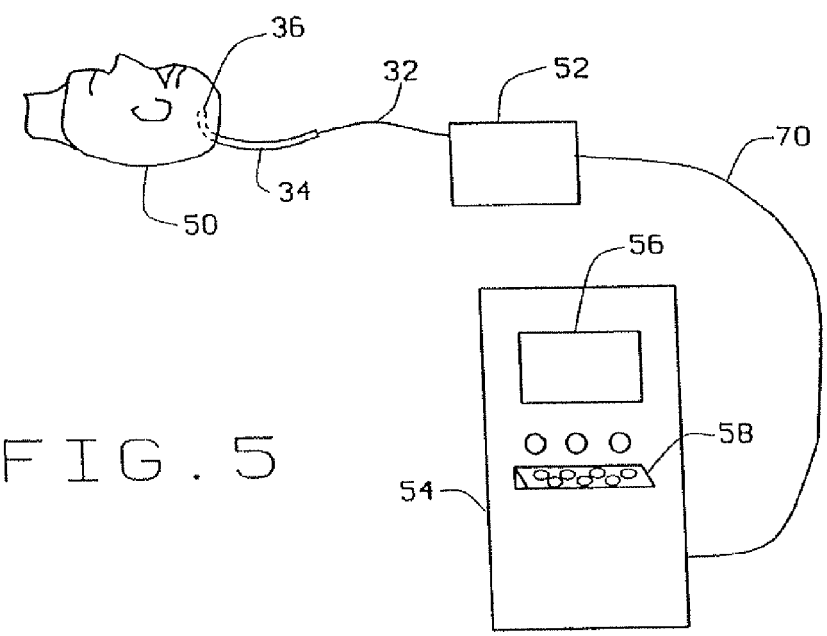
FIG. 5

METHOD AND APPARATUS FOR MAGNETICALLY CONTROLLING MOTION DIRECTION OF MECHANICALLY PUSHED CATHETER

CROSS-REFERENCE TO RELATED APPLICATIONS

This application is a continuation application of U.S. patent application Ser. No. 10/288,231, filed on Nov. 25, 2002, now issued U.S. Pat. No. 7,625,382, which is a continuation application of U.S. patent application Ser. No. 09/357,203, filed on Jul. 20, 1999, now issued U.S. Pat. No. 6,475,223, which is a divisional application of U.S. patent application Ser. No. 08/920,446, filed on Aug. 28, 1997, now issued U.S. Pat. No. 6,015,414. The entire disclosures of each of the above applications are incorporated herein by reference.

BACKGROUND OF THE INVENTION

1. Field of the Invention

This invention relates to devices and methods for moving an implant in a body, and more particularly to such devices and methods that apply pushing forces with a flexible attachment and that magnetically steer the implant in the body with high accuracy.

2. Description of Related Art

There is a large body of conventional (nonmagnetic) stereotactic prior art, in which a frame (e.g., a so-called "BRW Frame") is attached to the skull to provide a navigation framework. Such a frame has arcs to determine an angle of an "insertion guide" which is usually a straight tube through which some medical therapeutic agent is passed, such as a biopsy tool. These methods have been confined to straightline approaches to a target.

There is also a smaller body of prior art in which a handheld permanent magnet or an electromagnet is used to move a metallic implant.

Previous implants for delivering medication or therapy to body tissues, and particularly brain tissue, have generally relied upon the navigation of tethered implants within vessels, or navigation of tethered or untethered implants moved intraparenchymally (in general brain tissue) by magnetic force.

Navigation of untethered implants, in the past, has generally comprised finding ways to apply magnetic force optimally, including both magnitude and direction, for a given step of "free" motion. However, difficulty in finding a set of currents to accomplish a move step is encountered because of the complexity of calculating the magnetic forces resulting from multiple coils.

It is well-known that two like coils on a common axis, having like currents, provide a highly uniform magnetic field on their axis at the midpoint between them. In addition, it is known that the field is approximately uniform for an appreciable region around the midpoint, and relatively strong, as compared with any other two-coil arrangement having the same coil currents. This arrangement of coils and currents meets the need for an accurate, strong guiding torque applied to a magnetic implant near the midpoint between the coils. Because the field is quite uniform near the midpoint, undesired magnetic forces on the implant are negligible. However, this arrangement is less suitable for a moving implant when the implant is some distance from the midpoint between the coils or not on the axis, or when the implant axis is not along the coil axis. In these important cases, this simple coil arrangement cannot provide accurate directional guidance. Furthermore, simple vector combinations of three such coil pair arrangements cannot provide accurate guidance in an arbitrary direction, except at one spot at the center of the arrangement.

The Magnetic Stereotaxis System (MSS) originated from the hopes that a less-invasive methodology could be developed which would allow neurosurgeons to operate in previously inaccessible regions of the brain. By introducing a small permanent magnetic implant into the brain through a small "burr hole" drilled through the skull prior to the operation, large superconducting coils could be used in conjunction with a pushing mechanism to magnetically guide the implant and overlaying catheter through the brain's parenchyma, all the while avoiding the important structures of the brain. The operational methodology of the MSS was, and continues to be, expected to be less destructive to the tissues of the brain than the shunts, straight tubes, and other devices associated with conventional techniques in neurosurgery.

The first MSS was conceptually developed in 1984 as the Video Tumor Fighter (VTF), and is shown in U.S. Pat. No. 4,869,247 issued Sep. 26, 1989. This system specifically focused on the eradication of deep-seated brain tumors via hyperthermia-based treatment. It was envisioned that the magnetic coils of the VTF would guide a small (~3 mm diameter) magnetic thermosphere through the brain into a tumor. Rastering the implant throughout the volume of the growth, the tumor cells could be destroyed by inductively heating the implant with radio-frequency radiation.

Further studies revealed that the reality of a magnetomotive based system used to direct a small implant promised numerous applications other than the hyperthermia-based treatment of brain tumors by induction. These included: biopsy, pallidotomy, delivery of precision radiation therapy, magnetically placed implants that deliver chemotherapy to otherwise inaccessible tumor locations, and (by attaching a semi-permeable catheter to the implant) the delivery of chemicals to specific sites in the brain without the need for penetrating the blood-brain barrier which has complicated contemporary systemic chemical delivery. This means of chemical delivery seemed particularly hopeful in the treatment of Parkinson's disease, where the catheter could be used to deliver dopamine to the affected regions of the brain with minimal indiscriminate distribution of the neurotransmitter to the surrounding tissue, thereby lessening attendant side effects. It was in the light of these possible broadened applications of the VTF that the system became known as the MSS.

Referring now to FIG. 1A and FIG. 1B, the most recent MSS apparatus 10 included six superconducting coils (not visible in FIG. 1A and FIG. 1B) located in a rectangular box or helmet 12. With the z-axis defined in the direction of the axial component of the head, the x- and y-coil axes are rotated 45° from the sagittal plane 14 of the head, which would be positioned in opening 16. The x- and y-coil axes are symmetrically located such that the horizontal extensions 22 of the MSS apparatus 10 away from the patient's body is minimized. Because the lower edge of the treatable part of the brain is typically located 10 cm above the shoulder line for an average adult, the z-coils (located on the body-axis of the supine patient) were compressed to allow for a maximum extension of the head into helmet 12.

The vision component of the MSS consists of a superposition of pre-operative MRI images referenced by biplanar fluoroscopy cameras 20 linked to a real-time host system (not shown in FIG. 1A and FIG. 1B). Both cameras 20 are calibrated to the MSS six-coil helmet design. X-ray generators for cameras 20 are located inside magnetic shields 22. Using x-ray visible fiducial markers located on the skull of the conscious patient, the coordination of the implant's position inside the cranial volume to the helmet's reference system (and hence the corresponding preoperative MRI scan) is done through a series of coordinate transformations executed by a host system and displayed for the surgeon on a workstation.

The central problem to the inductively-based guidance of a magnetic implant pertains to the inverse problem of electromagnetism as influenced by Earnshaw's theorem. The conventional problem of electromagnetism centers on the evaluation of the gradient and magnetic field given established magnetomotive sources. For the MSS, however, the situation is reversed in that the magnetic field and its gradient are specified at a point in space while the strengths of the six actuators are to be determined. Control of the motion and position of an untethered implant would be difficult in the MSS, given the fundamental instability of a non-diamagnetic moment in a static or quasi-static magnetic field as related to Earnshaw's theorem for static/quasi-static magnetic fields, if it were not for the resistive nature of the parenchyma. In early tests, small cylindrical (up to 5 mm in length and 5 mm in diameter) permanently magnetized NdBFe objects were used. The relatively strong moment of these objects (0.016 A-m$^2$ to more than 0.04 A-m$^2$) facilitated the creation of the necessary aligning torque without the requirement of a strong magnetizing field, resulting in lower current values.

The permanent magnetization of the implant requires a predetermined magnetic field in order to ensure that the implant is oriented in the desired direction. While it is possible to generate a magnetic force to displace the implant, it was found that the requirement of specific force and field alignment could result in unobtainable currents (as high as thousands of amperes). It was also found that even for viable solutions, the equilibrium state was sometimes unstable to such an extent that the implant tended to be difficult to control.

SUMMARY OF THE INVENTION

The invention is an apparatus and method for moving an implant in the body by applying pushing forces with a flexible attachment and magnetically steering the implant in the body with high accuracy and controllability. Because the intended moving force is applied non-magnetically, it is possible and desirable to apply currents in the magnetic steering apparatus in such combinations as to maximize the magnetic field at a body location inside the coil array to thereby provide optimal directional guidance torque on an implant while minimizing undesired translational force on the implant.

According to one aspect of the invention, there is provided a method for controlling movement of a catheter through a medium, in which a flexible catheter having a magnetic tip is pushed through a medium, and a magnetic field having a magnitude and orientation effective to guide the mechanically-pushed catheter tip in a predetermined direction is applied.

According to another aspect of the invention, a method for providing stepwise movement of a catheter having a magnetic tip is provided, in which the method includes the steps of selecting a desired path of the catheter through living tissue, inserting the catheter tip into the living tissue, determining actual positions of the magnetic tip and correction vectors (the correction vectors representing differences between locations on the desired path and the actual positions of the magnetic tip), storing values of correction vectors in a memory, and applying a magnetic field adjusted to achieve movement of the magnetic tip at least approximately along the desired path, the adjustment depending upon at least one stored set of values of correction vectors.

Also provided is a device for guiding a catheter having a magnetic tip through a medium, the device comprising a helmet having a cavity configured to encompass a medium through which a catheter is to be guided, a magnetic field generator generating a magnetic field within the cavity, a position sensor sensing a location of a magnetic tip of a catheter in the cavity and generating a signal indicative of the sensed location, an advancement mechanism pushing the magnetic tip of the catheter through the medium, and a processor responsive to the signal from the position sensor and having an operator control input, the processor being configured to control the magnetic field generated by the magnetic field generator in response to commands input via the operator control input and the signal received from the position sensor.

The above embodiments may also incorporate significant additional improvements, including, for example, the minimization of a current metric, so that the proper magnetic field to guide the magnetic tip through the medium is generated with a near-minimum amount of current.

The methods and apparatuses of this invention provide the ability to more accurately direct a seed or catheter in the brain or other parts of the body, including the path to that position. Highly accurate directional guidance of implants is possible over arbitrary nonlinear paths, and the implant can be guided freely through tissues such as brain tissue, without being limited to the interior of vessels.

Additional advantages of the present invention over prior art systems are that:

(1) Solutions applicable to guiding an implant on a predetermined path are simpler, and thus, are found more rapidly and with less likelihood of error for a given step of motion.

(2) Solutions are much more stable than with prior art systems, and are free of runaway conditions.

(3) Currents applied by the new method are generally considerably smaller than with previous methods; therefore, the current changes between steps are smaller, allowing changes to be made much more rapidly and accurately between steps, and with less possibility of quenching superconducting magnets.

(4) Guidance force occurs without skid, which is a condition in which the magnetic field that orients the implant and the magnetic force are in different directions so that the axis of the implant skids along the path.

(5) Currents are applied in a simple temporal fashion, moving directly from one set to another set between two steps of motion. The actual force impulse causing each step of motion is from the duration and distance of the externally applied non-magnetic force during that step. (Prior art systems ramped currents from conditions for subthreshold force to that of a moving force and then back down below threshold at the appropriate time, which is a complex dynamic sequence subject to substantial error in step length due to the tribological nature of the implant and tissue.

(6) Navigation can now occur continuously rather than in steps.

It is thus an object of the invention to provide a method for controlling the motion of a catheter in any predetermined direction.

It is a further object of the invention to control the motion of a catheter by applying a torque to the catheter to guide its direction with a reliable, predictable strength.

It is yet another object of the invention to control the motion of a catheter rapidly, accurately, and reliably, even when the magnetic system used in conjunction with the catheter includes superconducting coils that are vulnerable to misoperation from too rapid current changes.

BRIEF DESCRIPTION OF THE DRAWINGS

FIG. 3A is drawing of a portion of a catheter having a metal tip, and FIG. 3B is a drawing of a magnetic element and push wire within the catheter of FIG. 3A;

FIG. 4 is a diagram showing various points and vectors along a desired path of a catheter tip, in which the points and vectors shown are significant for the calculation of the magnetic field needed to guide the tip in accordance with the invention;

FIG. 5 is a block diagram of a portion of a Magnetic Stereotaxis System in accordance with the invention;

DESCRIPTION OF THE PREFERRED EMBODIMENTS

The invention is described herein in the context of guiding an implant inside a brain because tests have been performed for this case. However, those skilled in the art will recognize that the invention is applicable to other parts of the body and to other media through which a magnetic tip at the end of a flexible catheter can be pushed.

Figure 1A:
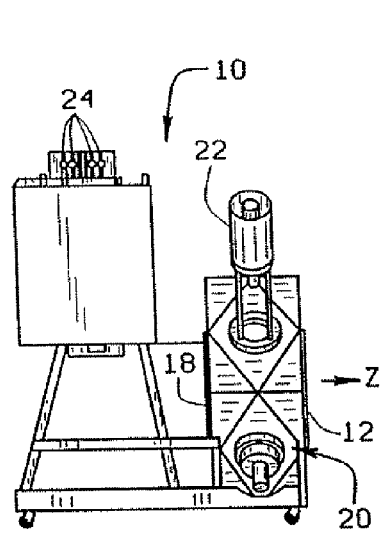
FIGS. 1A and 1B are views along the Z-axis and into the cavity of one embodiment of a Magnetic Stereotaxis System (MSS), respectively.
Figure 1B:
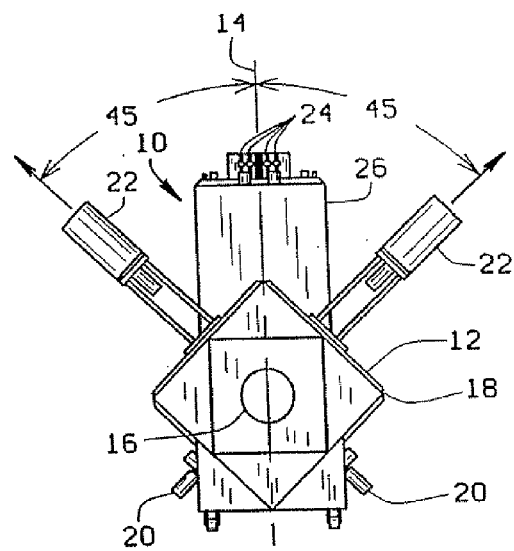
Figure 2:
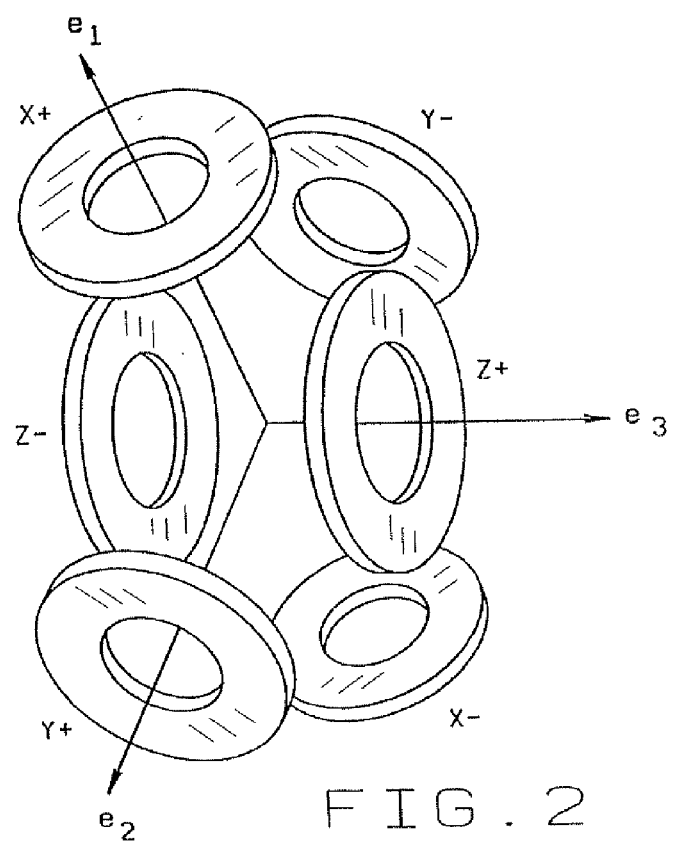
FIG. 2 is a simplified representation showing the orientation of superconducting coils within the helmet of an MSS.

In the present example, a system of six coils is provided. Referring to FIG. 2, which is a simplified representation of the coil geometry, the coils X+, X−, Y+, Y−, Z+, and Z− are operated in unbalanced pairs (X+, X−), (Y+, Y−), (Z+, Z−) acting approximately as three vectors X, Y, and Z having mutually perpendicular directions, but different magnitudes. The operation is achieved in a manner that is effective at positions off the axis of any or all of the three pairs of coils (X+, X−), (Y+, Y−), (Z+, Z−) constituting the helmet (or other coil support arrangement).

The method for controlling the path in the Magnetic Stereotaxis System (MSS) includes calculations involving vectors that represent desired path steps and corrective feedback vectors in an inventive adaptation of a well-known PID (proportional, integral, and derivative) feedback method. However, the operations here are on the motion of a magnetic implant. Referring to FIGS. 3A and 3B, the magnetic implant 30 acts as a leading element (the "directing train engine," which is called a magnetic delivery vehicle or MDV) and which is only part of the overall moving unit which also includes a pushing stylette 32 driven by a motor (not shown) which supplies a force F. Stylette 32 and implant 30 are surrounded by flexible catheter 34, which has a metal tip 36 at the end within which MDV 30 is located. The method and apparatus of this invention controls the curving elements of the catheter.

For the purposes of this discussion of the invention, the term "lag" is applied to the angle by which the catheter would fall outside a curve that would be followed by a completely limp catheter. During magnetic navigation, the MSS system monitors the position of the catheter tip (the MDV) versus a desired position in accordance with a planned path. Referring to FIG. 4, corrections are made in accordance with a feedback/lag model that is given by the equation $$V_{step}=V_{path}+V_{lag}+g(V_{correction}/|V_{correction}|), \quad (1)$$

in which:

$V_{lag}$ is a lag-correction vector pointing to an inside of a local curvature of the planned path indicated by R at point $p_2$; and g is a gain factor; and $V_{path}$ is constructed by finding a point $p_1$ on the planned path closest to the present actual position, and then finding a point $p_2$ further along the planned path which matches the length of the intended step. Then $V_{path}=p_2-p_1$;

$V_{correction}$ is a vector from the actual position to the point on the path closest to the present actual position (i.e., a direction opposite an "error vector"); and $V_{step}$ is the resultant direction that the next step should take, corrected for lag.

The direction of $V_{step}$ is constrained to vary from move to move in a manner so that sudden changes in $V_{step}$ result in a path having a specified minimum radius of curvature or a less curved trajectory. The value of g is computed and adjusted for each step by means of a PID model in which $$g=\|k_p V_{c(n)}+k_i(V_{c(n)}+V_{c(n-1)}+V_{c(n-2)})+k_d(V_{c(n)}-V_{c(n-1)})\|,$$
where:

$k_p$, $k_i$, and $k_d$ are predetermined constants that may be found by experiment; and $V_{c(n)}$, $V_{c(n-1)}$, and $V_{c(n-2)}$ are the correction vectors at the nth step (present step), the previous (n−1)th step, and the (n−2)th steps, respectively.

It is noted that what here is called a "correction vector" is the negative of what is often called an "error vector." The term "correction vector" rather than "error vector" has been used throughout this description for convenience. However, this usage is not intended to be limiting in any way, because those skilled in the art will recognize the equivalence of "correction vectors" and "error vectors" and the notational changes that would be required by the substitution of one for the other.

When the correction vectors at the nth, (n−1)th, and (n−2)th steps are used in the correction vector $V_{step}$, they become an approximation to an integral mode of control. That is, a correction is made proportional to the integral of the recent path errors. Similarly, an approximate derivative or rate correction is made when the difference ($V_{c(n)}-V_{c(n-1)}$) of the present and most recent correction vectors is used as a term in $V_{step}$.

In one exemplary MSS implementation, vector $V_{lag}$ was determined experimentally by attempting to drive a magnetic catheter tip (such as tip 36 in FIG. 3A) in a circle of predetermined radius, but setting $V_{lag}=0$. The catheter was driven by a motor providing a constant advancement rate through a phantom gel, which provided some friction. Where there is such friction, an equilibrium arises because the force from the gel counteracts the force from the magnetic field and tends to balance it at some point before alignment of movement with the magnetic field is achieved. In this case, the counterbalancing force of the gel simulated the counterbalancing force of actual brain tissue, and as expected, the magnetic tip spiraled outward from the circle in a direction a few degrees out of alignment with the magnetic field. $V_{lag}$ was then experimentally set to be the vector correction that would have been necessary to provide to counteract the deviation from the circular path.

By increasing the magnitude of the field, the magnitude of $V_{lag}$ can be reduced. However, it is also desirable to at least approximately minimize the coil currents required to generate the magnetic field. Experiments have shown that, for the particular set of coils in one MSS apparatus, with a motor pushing a catheter along the magnetic field at a rate of about 0.5 mm/s, there was little decrease in $V_{lag}$ for fields greater than about 0.3 Tesla. Therefore, in the experiment to determine $V_{lag}$, as well as in other tests, the magnetic field was constrained to have a magnitude no greater than 0.3 Tesla. This value has been found, by experiment, to be sufficient to orient the direction of movement of a magnetic tip of a catheter being pushed by a motor at 0.5 mm/s through a phantom gel. It will be understood that the necessary magnetic field magnitude may vary if different catheters, motors, or magnetic tips are used, or if a different advancement rate is applied.

Correction according to $V_{lag}$ is a single-parameter means of anticipating error that would occur due to restoring torques from an attached pushing element. A person skilled in the art would recognize the close relationship of this action to the concept of "feed-forward" in the field of control theory. It is intended, according to one aspect of the invention, that the inventive apparatuses and techniques may be useful for applications in which a simple feed-forward correction is not adequate. In such applications, a computer or processor will have a representation of a planned or predetermined path stored in its memory. At any location or locations where the planned path deviates from a straight line in front of a then-present location of the seed, a program stored in the computer provides an added correction vector, which may be a function of several different parameters, to provide a better correction than $V_{lag}$ by anticipating future error in the absence of such correction. As one example, if a planned path curves in more than one plane, a correction vector can contain terms which have correction vector components in each of the planes. The weighting of these components preferably varies as the inverses of the individual radii of curvature, and are also preferably weighted inversely according to the distance from the present seed position at which the particular curvatures occur. These parameters can be readily calculated by a program stored in the memory of the computer. It is thus possible, and may be preferable, to use information related to a future location of the seed to guide the seed, and/or a determined rate of change in the observed correction vectors in addition to information stored in memory about its past position and errors.

With respect to the gain parameters $k_p$, $k_i$, and $k_d$, it has been experimentally determined that, for the tested MSS apparatus, it is sufficient to set $k_p$=0.5, $k_i$=0.5, and $k_d$=0. The parameter $k_d$, which effectively adjusts the speed of response of the system, can be set to zero because the system response obtained has been satisfactory for the relatively slow tip advancement rate of 0.5 mm/s. In addition, setting $k_d$=0 has the advantage of reducing noise in the system, because the imaging method used to locate the magnetic tip (biplanar xray imaging) has provided an accuracy only within about +/−1.0 mm. Adjusting the system gain by increasing the magnitude of $k_d$ would result in significant noise amplification without a concomitant increase in position sensing accuracy. If more accurate methods of determining the location of the seed were used, it would be practical to use a nonzero value of $k_d$ to provide more rapid system response. This more rapid system response could permit an increase of the tip advancement rate above 0.5 mm/s in appropriate medical procedures, which may shorten the time necessary to perform such procedures.

Once the vector $V_{step}$ is determined, representing a vector corresponding to a motion of the magnetic tip at least approximately in the direction of the desired path, the coil currents necessary to generate the required field must be determined. In general, this problem is underdetermined in that many different sets of coil currents could be used to generate the required field, and, without the addition of further constraints, solutions can be obtained that require impractical amounts of currents in some or all of the coils. A method of determining practical values of coil currents that generate a sufficient magnitude magnetic field in the correct direction at the location of the magnetic tip has been found, and is described herein.

For controlling superconducting or normally conducting coils, the root-mean-square value of the coil currents (the coil-current metric) is minimized while the strength and direction of the magnetic field remain at the desired values. (The magnetic field is linear with respect to the coil currents.) This constraint removes three of the six degrees of freedom in selecting the six coil currents, leaving a quadratic equation for the current metric. This metric is minimized to compute the optimal coil currents. While minimizing the current metric does not necessarily correspond to minimizing the individual current magnitudes, it is a useful and efficient way of ensuring that the current magnitudes are kept at a sufficiently low level for purposes of the invention.

The m equality, linearly constrained quadratic problem is stated as $$\text{Maximize } z = \sum_{i=1}^{n} x_i c_i + \sum_{i,j=1}^{n} x_i P_i I_{ij} x_j \quad \text{subject to } \sum_{j=1}^{n} D_{ij} x_j = e_j \quad (i = 1, \ldots, m) \qquad (2)$$

or $$\text{Maximize } z = x^T c + x^T P x \quad \text{subject to } Dx = e$$

where $x \in R^n$. We assume that the conditions $Dx=e$ comprise a non-degenerate set with $m<n$. If $m>n$, then the system is over specified and no solution may occur. In the case that $m=n$, then one solution exists at the point $x_o=D^{-1}e$ providing $|D| \neq 0$. Hence, no optimization is possible or necessary.

Constructing the Lagrangian, we find that $$L = x^T c + + x^T P x + \lambda^T (Dx - e) \qquad (3)$$

where m Lagrange multipliers have been introduced. From the Lagrangian, we we obtain the global extremum $$\begin{Bmatrix} x_o \\ \lambda_o \end{Bmatrix} = \begin{Bmatrix} 2P & D^T \\ D & 0 \end{Bmatrix}^{-1} \begin{Bmatrix} -c \\ e \end{Bmatrix} \qquad (4)$$

where it is assumed that the matrix inversion is possible.

To particularize this result to the minimization of the current metric for the MSS, we begin by focusing solely on the static and quasi-static cases, thus assuming that the source currents are either held constant or ramped relatively slowly in time. Given n magnetomotive sources (or, in this sense, actuators), we wish to operate the sources with minimal currents so that a desired magnetic field may be specified for a selected point in space $x_o$ where $x_o \in R$. The total magnetic field at any point x, b(x), is the linear superposition of the magnetic fields due to each source evaluated at x:

$$b(x) = \Sigma_{i=1}^{n} b_i(x) \qquad (5)$$

Since $b_i(x)$ is linear with respect to its corresponding source current, $I_i$, the above may be written as $$b(x,I) = \Sigma_{i=1}^{n} B_i(x) I_i \qquad (6)$$

where $B_i(x)$ consists of the three current-independent components of the magnetic field for each source. If we define the 3×n matrix $B(x)$ as $$B(x)=\{B_1(x)|B_2(x)|\ldots|B_n(x)\} \quad (7)$$

and we write the currents as the n-element column vector I, then Eq. (6) and Eq. (7) can be combined to form the matrix relationship $$b(x,I)=B(x)I \quad (8)$$

Note that n>3 is assumed in order for an optimization to be made for a desired magnetic field b (which consists of three components). If n<3 (i.e., two actuators or less), the system is over constrained and no solution exists unless there is a degeneracy in Eq. (8). If n=3, then the solution to the currents, $I_o$, is given by $I_o = B^{-1}(x_o)b$.

We now focus our attention on the current metric defined as $$z(I) = \Sigma_{i=1}^n I_i^2 = I^T I \quad (9)$$

While the metric does not specifically limit the individual currents, it does serve as a means of penalizing those solutions that are associated with strong currents. The problem of finding an optimal set of currents (for n>3 sources) may now be stated in a form for which there are m=3 equality constraints:

Maximize $z(I)=-I^T I$, subject to $B(x_o)I=b$ (10)

It is noted that we could just as easily minimize the current metric above without loss of generality; however, writing the problem in the form of Eq. (10) is convenient for our present purposes. Since the metric of Eq. (10) is a concave function, the solution for the currents is:

$$\begin{Bmatrix} I_o \\ \lambda_o \end{Bmatrix} = \begin{Bmatrix} 2I_D & B(x_o)^T \\ B(x_o) & 0 \end{Bmatrix}^{-1} \begin{Bmatrix} 0 \\ b \end{Bmatrix} \quad (11)$$

where $I_D$ is the identity matrix. Inspection of Eq. (10) reveals that only one extremum (and hence, the global maximum) of the negative current metric can occur. Eq. (11) thus provides the solution for the coil currents $I_o$ in the MSS given a specified magnetic field.

While the current metric is sufficient in restricting the currents to small values in most cases, it does not minimize them. It is possible that a larger metric results when smaller currents are distributed over several sources. For example, say the desired field for a four source system corresponds to the optimal set of currents $I_o^T=\{10\ 80\ 10\ 80\}$(A) for which $z(I_o)=13000\ A^2$. If the individual currents must be less than 75 A, another (possibly more useful solution in some cases) would correspond to $I_o^T=\{60\ 70\ 60\ 70\}$(A), for which $z(I_o) = 17000\ A^2$, providing the currents generate the same magnetic field. Including the k linear current limits $DI \geq e$ into Eq. (10), our general n-source, linearly constrained problem is stated as Maximize $z=-I^T I$, subject to $B(x_o)I=b$ and $DI \geq e$ (12)

Since it is more commonly found that the n actuators possess upper and lower limits according to $|I_i| \geq I_{max}$ (i=1, ..., n), the constraints form a closed and bounded set providing the specification of B still holds for the range of allowed currents. The problem becomes Maximize $z(I) = -I^T I$, subject to $B(x_o)I$ (13)

$$= b \begin{Bmatrix} I_D \\ -I_D \end{Bmatrix} I \geq -\begin{Bmatrix} I_{max} \\ I_{max} \end{Bmatrix}$$

where k=2n inequality constraints with $I_{max,i}=I_{max}$ for i=1, ..., n have been introduced. The conditions that must be satisfied in order for maximum to exist are given by $$\begin{rcases} -2I_o + \mu_o^T \begin{Bmatrix} -I_D \\ I_D \end{Bmatrix} + \lambda_o^T B(x_o) = 0 \\ \mu_o^T \left( \begin{Bmatrix} -I_D \\ I_D \end{Bmatrix} I_o + \begin{Bmatrix} I_{max} \\ I_{max} \end{Bmatrix} \right) = 0 \\ B(x_o) = b \\ -I_{max} \leq I_o \leq I_{max} \\ \mu_o \geq 0 \end{rcases} \quad (14)$$

The possible $2^{2n}=4^n$ solutions of the above set of equations follow from Eq. 29 of Appendix B where individual constraints are activated among the 2n inequality conditions. As was previously discussed, when the activated constraints combined with the equality constraints outnumber the degrees of freedom, the system of equations become over specified and no solution need be calculated. For those cases in which the system of equations is exactly specified, the solution must be checked against the inequality constraints to deem it viable. There remain $$4^n - \Sigma_{i=n-3}^{2n} 2n!/((2n-i)!i!)$$

of the $4^n$ cases which can be solved (assuming a solution exists). Those solutions that satisfy the constraints are saved and the set that results in the maximum value of $z(I_o)=-I_o^T I_o$ [or minimum of $z(I_o)=I_o^T I_o$] is reported as the optimal solution.

It is sometimes useful to restrict the magnetically generated force on a small permanent moment. For example, quasistatic systems such as magnetic suspensions and the MSS can profit from an inclusion of force constraints if higher currents are acceptable. The force at $x_o$, $f(x_o)$, generated on a small permanent magnetic moment, m, due to a magnetic field, b, is given by $$f(x_o) = \Delta(m^T b(x))|_{x=x_o} \quad (15)$$

An easier notation for the present purposes involves writing the three component of the force as $$f_i(x_o) = m^T(x_o) \partial b/\partial x_i \ (i=1,2,3) \quad (16)$$

For those problems in which the moment is allowed to align with the magnetic field [i.e., $m=b(x_o)\|m\|/\|b\|$], Eq. 16 is transformed into $$f_i(x_o) = \frac{\|m\|}{\|b(x_o)\|} b(x_o)^T \left( \frac{\partial b(x)}{\partial x_i} \right)\bigg|_{x=x_o} \ (i=1,2,3) \quad (17)$$

where the strength of the moment $\|m\|$ is known. Combining the results of Eq. (17) with Eq. (8), a somewhat complicated problem arises for those cases in which the orientation of the magnetic field at $x_o$ is unrestricted. This can be seen in the nonlinear form of $$f_i(x_{o,I}) = \|m\| \frac{I^T B(x_o)^T \left(\frac{\partial B(x_o)}{\partial x_i}\right) I}{\sqrt{I^T B(x_o)^T B(x_o) I}} \quad (i = 1, 2, 3) \tag{18}$$

For the present purposes, only those cases that rely on a specified magnetic field are considered.

Using the current dependence of the magnetic sources and a predetermined magnetic field b where $b = B(x_o)I$, Eq. (17) can be written in two forms. The linear and quadratic forms are given by, respectively, $$f_i(x_{o,I}) = \frac{\|m\|}{\|b\|} b^T \left(\frac{\partial B(x_o)}{\partial x_i}\right) I \quad (i = 1, 2, 3) \tag{19}$$

and $$f_i(x_{o,I}) = \frac{\|m\|}{\|b\|} I^T B(x_o)^T \left(\frac{\partial B(x_o)}{\partial x_i}\right) I \quad (i = 1, 2, 3) \tag{20}$$

While the form of Eq. (19) may appear more useful, at least seven actuators must be present in order to overcome the six constraints due to the specification of the magnetic field and force. If it is important that both the force and field be specified and if there are a sufficient number of actuators, then the work follows from Eq. (10)-Eq. (14) with the three additional force constraints being included into the field constraints. If there are exactly six actuators, then there exists a unique solution to the problem at $$I_o = \begin{pmatrix} \frac{\|m\|}{\|b\|} \Delta(b^T B(x))_{x=x_o} \\ B \end{pmatrix}^{-1} \begin{pmatrix} f \\ b \end{pmatrix} \tag{21}$$

providing the operating matrix is invertible and the currents are unbounded.

More often than not, the experimenter is more concerned with either minimizing a component of the force or the strength of the force with respect to a limited range of currents and a desired magnetic field rather than specifying a specific value of the force. If examining a component of the force, Eq. (20) is generalized so that the force along the unit vector $\mu(\|\mu\|=1)$ is minimized. The force component of interest becomes $\mu^T f(x_o, I)$ and the problem is written as $$\text{Maximize } z(I) = \mu^T f(x_o, I) = -\frac{\|m\|}{\|b\|} \begin{pmatrix} \sum_{i=1,2,3} \mu_i I^T B(x_o)^T \\ \left(\frac{\partial B(x_o)}{\partial x_i}\right) I \end{pmatrix} \tag{22}$$

$$\text{Subject to: } B(x_o)I_o = b$$

$$\begin{Bmatrix} I_D \\ -I_D \end{Bmatrix} I \geq -\begin{Bmatrix} I_{max} \\ I_{max} \end{Bmatrix}$$

Likewise, if the force strength is to be minimized, a quadratic form is obtained for the objective function by squaring the force components of Eq. (19):

$$\text{Maximize } z(I) = -f(x_o, I)^T f(x_o, I) \tag{23}$$

$$= -\left(\frac{\|m\|}{\|b\|}\right)^2 \begin{pmatrix} \sum_{i=1,2,3} I^T \left(\frac{\partial B^T(x_o)}{\partial x_i}\right) \\ bb^T \left(\frac{\partial B(x_o)}{\partial x_i}\right) I \end{pmatrix}$$

$$\text{Subject to: } B(x_o)I_o = b$$

$$\begin{Bmatrix} I_D \\ -I_D \end{Bmatrix} I \geq -\begin{Bmatrix} I_{max} \\ I_{max} \end{Bmatrix}$$

If it is desired that the force be maximized rather than minimized, then the negative sign to the objective function is left off in Eq. (22) and Eq. (23). The conditions that establish the existence of a minimum or maximum follow from Eq. 27 of Appendix A. Note that only for force minimizations may the currents be left unbounded.

Portions of the above description of hardware and control methods and apparatuses refer to a six-coil system for use in certain applications in the medical field. However, the invention is not limited to systems having any particular number of coils, and is suitable for applications (including magnetic surgery applications) for which other coil numbers and arrangements may be preferable. For example, it is possible to remove the front coil of the above system, and to bring side coils closer together. The resulting five-coil arrangement would allow the patient to be more accessible to a surgeon, an important consideration for some surgical procedures. Other arrangements with different numbers of coils may be particularly useful with some other types of operations, for example, those at locations in the body other than the head. (It should be noted that it is not required by the invention that embodiments of multiple coil systems necessarily have coils that are operated in pairs, opposed or otherwise. Thus, the invention also encompasses systems having arbitrary numbers of coils.)

Figure 6:
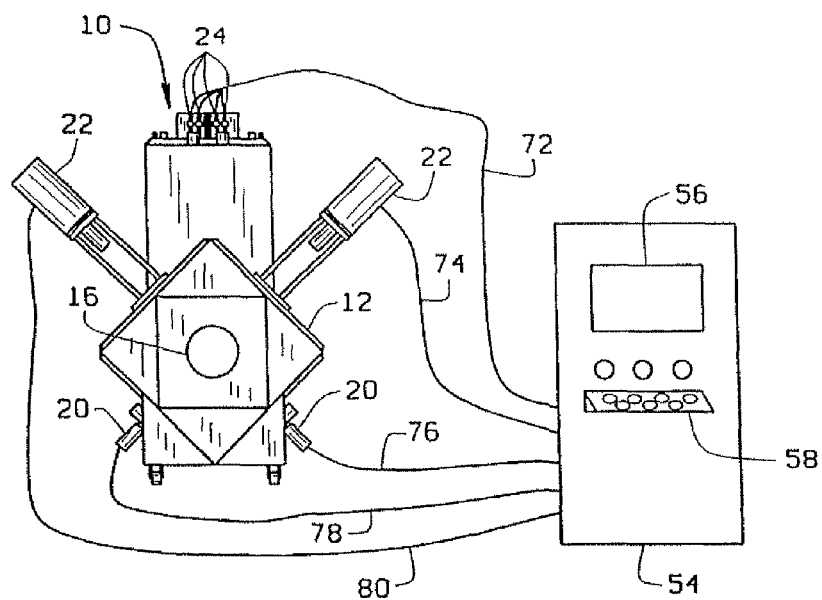
FIG. 6 is a block diagram of another portion of the Magnetic Stereotaxis System of FIG. 5.

An apparatus that controls coil currents and magnetic tip advancement is illustrated in block diagram form in FIG. 5 and FIG. 6. (It should be noted that not all external connections to console 54 are shown in each figure.) FIG. 5 shows a catheter 34 with metal tip 36 having a magnetic implant 30 inside (see also FIG. 3A). This catheter is shown with tip 36 already implanted in the brain of a patient 50, at the beginning stages of a medical procedure. Push wire 32 is operatively coupled to a motor in an advancement mechanism 52 that a surgeon may control by issuing commands at a console 54. Console 54 includes a real-time computer having a display screen 56 and an operator control 58, which may be a keypad or other convenient data entry device. Although the apparatus is described in conjunction with operations on a catheter in the brain of patient 50, it should be recognized that the inventive apparatus and techniques may be applied to other living tissues as well, or in other media, living or not, through which it may be desired to push a magnetic tip on a flexible push wire or guide wire.

Referring now to FIG. 6, the head of patient 50 (not shown in FIG. 6) is disposed in opening 16 of coil apparatus 10, as the surgeon operates the inventive apparatus. Console 54 contains a processor such as a digital computer responsive to operator commands input through operator control 58 and to cameras 20 for controlling a power supply (not shown) that supplies currents to coil terminals 24 to generate the required magnetic fields. To fully automate the catheter movement, advancement mechanism 52 may also be controlled by the processor. Cameras 20 and X-ray generators inside magnetic shields 22 provide magnetic tip position information to the processor in console 54. It will be recognized, however, that other suitable means for providing position information may be substituted for the cameras 20 and X-ray generators.

To perform a procedure, a surgeon would observe the initial position of the magnetic tip 36 with the aid of console 54 and plan a path through the tissue of patient 50 (in this case, the brain) to a point at which treatment is to be delivered. The surgeon may also choose a step size and an advancement rate, although either or both of these may be preprogrammed. The surgeon then activates the system by issuing appropriate commands through console 54.

In response to these commands, the processor inside console 54 computes positions of metal tip 36 from data received from cameras 20, as well as vectors $V_{step}$ and the coil currents necessary to move metal tip 36 along the desired path at the beginning of each step, and applies the computed currents to the coils while advancement mechanism 52 advances metal tip 36 through the tissue. Correction vectors $V_{correction}$ are stored in memory to provide the necessary history for the PID calculations. The advancement continues until the endpoint of the path is reached. Although the advancement occurs in steps, the positions and coil currents can typically be calculated rapidly enough to make the advancement of magnetic tip 36 essentially continuous.

If necessary, the surgeon may intervene by stopping movement of the catheter or by changing its course before the originally planned endpoint is reached. When a course change is made, the correction vectors V correction stored in the memory of the processor during advancement on the aborted path are either cleared from memory or simply ignored so that these vectors do not influence the calculations performed to direct the magnetic tip along the new path.

Figure 7:
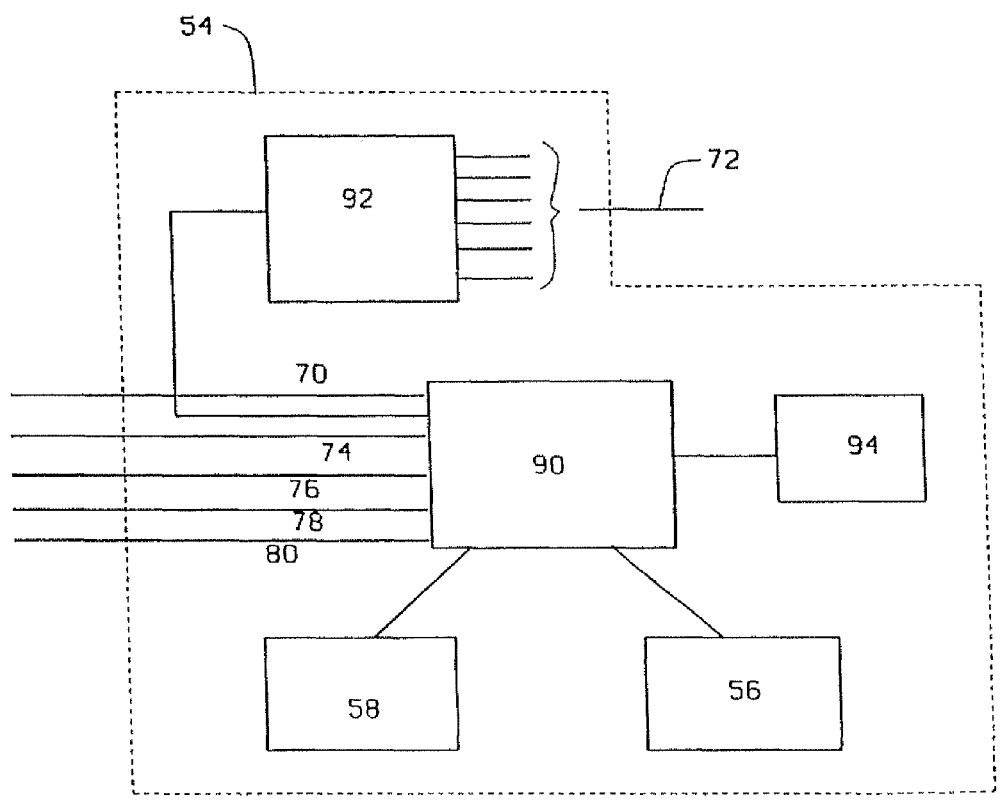
FIG. 7 is a block diagram of a configuration of a processor suitable for use in the MSS of FIGS. 5 and 6.

FIG. 7 shows a simple block diagram of a manner in which a processor 90 may be configured for use in console 54. Processor 90 is provided with operator control 58 (which may, for example, be a keyboard) for accepting operator input and a display 56 for displaying information to the operator. Inputs and outputs 70, 74, 76, 78, and 80 corresponding to those shown in FIG. 5 and FIG. 6 are provided to obtain data required for sensing position of the catheter tip and for controlling the X-ray fluoroscopes and superconducting coils inside helmet 12. A random access memory 94 is provided for storing values of $V_{correction}$, and a programmable power supply 92 is provided to supply current to the superconducting coils through a plurality of lines 72 in accordance with the current values computed by processor 90. Although programmable power supply 92 is shown as a power supply having multiple, independent, programmable outputs, it will be readily appreciated that a plurality of individual power supplies may be used as an alternative to the power supply shown in the figure.

A document describing the structure of a computer program to operate a processor in accordance with the invention is attached as Appendix A. Computer programs written in the C++ computer language that determine and control current applied to the coils in accordance with the invention appear in Appendix B. A more detailed treatment of quadratic optimizations pertaining to current solutions for magnetic field sources appears in Appendix C. A more detailed treatment of the generation of a magnetic field for a circular coil of distributed current appears in Appendix D. A detailed mathematical treatment of the summation of field components for single and multiple coils appears in Appendix E, which continues the discussion of the material in Appendix D.

The above-described embodiments are intended to be illustrative only. For example, there are numerous types of magnetic surgery procedures for which the coil systems described and the method of calculating and providing currents to generate fields and forces are important, but for which there is no planned or predetermined path and no feedback. Instead, a device in accordance with the general principles of the invention can provide magnetic guidance of a tip of a surgical device such as a catheter, endoscope, etc. The invention can be readily adapted so that a surgeon, under guidance from an imaging system, uses the magnetic system to negotiate otherwise difficult turns and movements of the surgical device as he or she pushes a device along the interior of a vessel. It will also be recognized that many of the inventive methods and apparatuses may be used in conjunction with any coil in a non-resonant circuit that applies a magnetic force on a suspended or embedded object that is magnetically moveable. Many other modifications falling within the spirit of the invention will be apparent to those skilled in the art. Therefore, the scope of the invention should be determined by reference to the claims below and the full range of equivalents in accordance with applicable law.

What is claimed is:

1. A method for controlling movement of a catheter through a body, the method comprising the steps of:
    (a) mechanically pushing a flexible catheter having a magnetic tip through the body to advance the medical device; and
    (b) while the medical device is being advanced, applying with at least one electromagnet outside the body a magnetic field having a magnitude and an orientation effective to orient the magnetic tip of the mechanically-pushed catheter in a predetermined direction.

2. The method of claim 1 and further comprising the steps of sensing catheter tip positions, and adjusting the applied magnetic field so that the catheter tip advances stepwise at least approximately along a predetermined path.

3. The method of claim 1 and-further comprising the steps of:
    sensing catheter tip position;
    generating a signal indicative of the position of the catheter tip;
    determining a correction vector between the position of the catheter tip and the predetermined path at least partially in response to said generated signal; and
    adjusting the applied magnetic field at least partially in response to the determined correction vector so that the catheter tip advances at least approximately along a predetermined path.

4. The method of claim 3 further comprising the step of storing correction vectors in a memory, and wherein the determining step comprises determining the adjustment at least partially in response to a presently-determined correction vector and at least one of the previously stored correction vectors.

5. The method of claim 1 wherein the step of applying a magnetic field comprises the step of applying currents to a plurality of superconducting coils.

6. The method of claim 5 wherein the currents are selected to minimize a predetermined current metric.

7. The method of claim 5 wherein the currents are selected to minimize a current-limiting constraint set.

8. The method of claim 1 wherein the step of mechanically pushing the catheter comprises the step of pushing the catheter through living tissue.

9. The method of claim 8 wherein the living tissue is human brain tissue.

10. The method of claim 8 further comprising the steps of sensing catheter tip positions, and adjusting the applied magnetic field so that the catheter tip advances stepwise at least approximately along a predetermined path.

11. The method of claim 10 further comprising the steps of:
generating a signal indicative of the position of the catheter tip;
determining a correction vector between the position of the catheter tip and the predetermined path at least partially in response to said signal;
and wherein the adjustment step comprises determining the adjustment to the applied magnetic field at least partially in response to the determined correction vector.

12. The method of claim 11 further comprising the step of storing correction vectors in a memory, and wherein the determining step comprises determining the adjustment at least partially in response to a presently-determined correction vector and at least one previously stored correction vector.

13. The method of claim 11 further comprising the step of storing correction vectors in a memory, and wherein the determining step comprises determining the adjustment at least partially in response to a rate of change of correction vectors in a previous step.

14. The method of claim 11 further comprising the step of storing correction vectors in a memory, and wherein the determining step comprises determining the adjustment at least partially in response to an anticipated future error with respect to a planned path.

15. The method of claim 8 wherein the step of applying a magnetic field comprises the step of applying currents to a plurality of superconducting coils.

16. The method of claim 15 wherein the currents are selected to minimize a predetermined current metric.

17. The method of claim 15 wherein the currents are selected to minimize a current-limiting constraint set.

* * * * *